US012648764B2

(12) United States Patent
Alravvi et al.

(10) Patent No.: US 12,648,764 B2
(45) Date of Patent: Jun. 9, 2026

(54) HVS AND PAP SMEAR TESTING APPARATUS

(71) Applicant: Omar Alravvi, Fatih/Istanbul (TR)

(72) Inventors: Omar Alravvi, Fatih/Istanbul (TR);
Aeshah Omar Mahmood Al-Rawe,
Fatih/Istanbul (TR); **Abu-Baker Omar
Mahmood Al-Rawe**, Fatih/Istanbul
(TR); **Othman Omar Mahmood
Al-Rawe**, Fatih/Istanbul (TR)

(73) Assignee: Omar Alravvi, Fatih/Istanbul (TR)

( * ) Notice: Subject to any disclaimer, the term of this
patent is extended or adjusted under 35
U.S.C. 154(b) by 1202 days.

(21) Appl. No.: 16/960,668

(22) PCT Filed: Apr. 20, 2018

(86) PCT No.: PCT/TR2018/050182
§ 371 (c)(1),
(2) Date: Jul. 8, 2020

(87) PCT Pub. No.: WO2019/139547
PCT Pub. Date: Jul. 18, 2019

(65) Prior Publication Data
US 2020/0330083 A1      Oct. 22, 2020

(30) Foreign Application Priority Data
Jan. 9, 2018    (TR) ................................. 2018/00276

(51) Int. Cl.
A61B 10/02          (2006.01)
A61B 10/00          (2006.01)

(52) U.S. Cl.
CPC .. A61B 10/0291 (2013.01); A61B 2010/0074
(2013.01); A61B 2010/0216 (2013.01)

(58) Field of Classification Search
CPC .... A61B 2010/0074; A61B 2010/0216; A61B
10/0291; A61B 10/02; G01N 2001/028
See application file for complete search history.

(56)                References Cited

U.S. PATENT DOCUMENTS

2005/0284239 A1    12/2005  Chuang
2007/0106174 A1*    5/2007  Sanders ................. A61B 17/42
                                                    604/38
(Continued)

FOREIGN PATENT DOCUMENTS

CN          205027584 U    2/2016
WO      WO-01/01867 A1    1/2001
WO   WO-2008/012847 A1    1/2008

*Primary Examiner* — Jennifer Robertson
*Assistant Examiner* — H.Q. Nguyen
(74) *Attorney, Agent, or Firm* — Maier & Maier, PLLC

(57)                ABSTRACT

The subject invention is related to the HVS and Pap smear
testing apparatus providing Pap smear testing for Human
Papilloma Virus (HPV) and HSV test for culture and sen-
sitivity by doctor and patient automatically and being char-
acterized by outer cylinder (1), head (2), interior side (3),
end side (4), ring 1 (5), spiral end (6), ring 2a (7), internal
cylinder 1 (8), piston cover (9), cylinder (10), protective
cover (11), end part (12), outer end side (13), interior end
side (14), flexible tube (15), medical tube (16), spring 1 (17),
recoil cylinder 1 (18), line 1 (19.*a*), line 2 (19.*b*), ring 3 (20),
ring 2b (21), spring 2 (22), internal cylinder 2 (23), ring 4
(24), hole 1 (25), tip holder (26), spring 3 (27), recoil
cylinder 2 (28), hole 2 (29), circle 1 (30), coil (31), ring 5
(32), ring 6 (33), head bar 1 (34), cotton (35), empty space
(36), accuracy sign (37), cone (38), circle 2 (39), black
rubber (40), rear part (41), small cylinder 1 (42), wing (43),
small cone (44), small cylinder 2 (45), head bar 2 (46), brush
(47), ring 7 (48), brush bristle (49), sharp edge (50), and hole
3 (51).

11 Claims, 12 Drawing Sheets

(56)         References Cited

U.S. PATENT DOCUMENTS

| 2007/0287158 A1* | 12/2007 | Gorodeski ....... G01N 33/57442 |
| | | 435/6.12 |
| 2008/0045924 A1* | 2/2008 | Cox ...................... A61B 17/42 |
| | | 604/515 |
| 2009/0082695 A1* | 3/2009 | Whitehead ......... A61B 1/00052 |
| | | 600/572 |
| 2011/0004122 A1* | 1/2011 | Sangha .............. A61B 10/0045 |
| | | 600/572 |
| 2011/0087133 A1 | 4/2011 | Ching et al. |
| 2011/0105953 A1 | 5/2011 | Lai |
| 2013/0066233 A1* | 3/2013 | Klein ................ A61B 10/0291 |
| | | 600/572 |
| 2016/0262734 A1 | 9/2016 | Chin-Ly |

* cited by examiner

HVS AND PAP SMEAR TESTING APPARATUS

TECHNICAL FIELD

The subject invention is related to a HVS and Pap smear testing apparatus which provides convenience for women themselves, or for doctors, to be able to take cervical cell sample or liquids (materials) from the vagina for Human Papilloma Virus (HPV) diagnosis and cultural sensitivity.

BACKGROUND

The cervix is the zone where uterus and vagina are united and contains the lower part of the uterus in the human female reproductive system. Looking at the cervix from the vagina, it is in the shape of a hemisphere at the end of the vagina. The cervix is the narrow cervical area of the uterus opening to the vagina. It has a very strong muscle structure. It is very tight and closed and may open only during giving birth. The cervix also helps prevent infections from reaching the uterus and serve as an important barrier.

Human Papilloma Virus (HPV) is one of the most common infections that are sexually transmitted. The HPV virus settles on the penis in men and on the bulb, outer sexual organs, and cervix in women. When the HPV virus enters the body, it settles in the cells and is named recurrent genital wart (condyloma). The symptoms thereof are warts appearing on hands and feet, respiratory tract, and venereal area. It is known that there are hundreds of different sub-groups of this virus and some of these groups cause cervical cancer.

HPV infection is the most common and seen at every age. The person contracting an HPV infection has not acquired immunity to this virus. There are two reasons why the body fails to acquire immunity:

The body is unable to respond against infection strongly and therefore the immune system of the person fails to provide long term protection. The human body may face the infection risk again for the same HPV type.

HPV virus or the particles belonging to the virus do not mix with blood and is/are found in the cell. Therefore, it does not form an immunity to create any memory.

Cervical cancer becomes a disease with a substantially high probability to recover at the stage of lesion prior to cancer or when contacted at a very early stage. Early diagnosis and treatment in this disease are very important. The incubation period of cervical cancer is very long. The period from appearance of lesions which are the precursor of cancer in cells to the formation of cancer varies between 5-10 years and is longer in certain cases.

Against cervical cancer, smear testing is conducted for control of the HPV infection. The purpose of this test is to know about cervical cancer and early diagnose the lesions. The smear test is known also as Papanicolaou test, Pap test, cervical smear test, cervical swab and cervical cytology. This test is carried out with routine controls since it has the effect of saving human life.

An HVS test consists of taking samples of vaginal secretion by means of a device similar to a cotton gemma. The swab being released is then placed into a special container and sent to a microbiology laboratory for a more advanced analysis. Laboratory technicians attempt to create an artificial environment which is suitable for reproduction of bacteria. Therefore, "culture and sensitivity" simply refers to the testing process used in order to determine the necessity for definition of the bacteria in a sample and then which antibiotics to be removed. This method is used commonly in microbiology in testing various samples like various bodily discharges into urine samples for "culture and sensitivity." Obstetricians send the sample taken directly from the liquid for microbiological analysis. Vaginal secretions are then dyed and examined under microscope.

In the existing technique, a Pap smear test is used as the device for collecting a sample in order to be used only by doctors during gynecological examination of patients in general. For a smear test, the cells discharged from the cervix to the vagina by means of an ayre spatula or cytological brushes during gynecological examination are collected. Furthermore, a swab is taken form cervix by means of cytological brush. In the existing technique, since the device used for collecting sample is required to reach the squamacolumnar junction (SCJ), namely, the area where squamous epithelium (flat) laying the outer section of cervix and columnar (cylindrical) cells laying the canal of cervix conjoin. However, this is difficult for collecting rod-type cells. Additionally, when a user is using the device, since he/she will not be able place the device to the SCJ zone correctly and, in case he/she inserts the device to a very deep area in the body cavity when he/she tries to place the device, there may be injuries. For this reason, it is required to consult with a professional, e.g., a doctor, for assistance in general. Therefore, in known techniques, a Pap smear test made by a doctor in this way is very laborious and time-consuming. Furthermore, for women to be able to have a Pap smear test made on a regular basis, a sufficient level of access to healthcare institutions or facilities is needed.

In the existing technique, when the sample taken from cervix is withdrawn and when being placed onto lam, there is the probability of sample contact with the doctor or some other place. Furthermore, in order for the sample taken not to dry out, or for cell forms not to incur damage, the sample is required to be sent to a laboratory. However, according to the claimed invention, a self-automatic HVS and Pap smear test apparatus that may be used by a doctor may be taken to laboratory environment without the risk of contact. The claimed invention is capable of being self-administered by a patient or administered by a doctor, and allows for collecting the cells readily. In particular, a Pap smear search can be used for taking a high vaginal swab for culture and sensitivity and for early diagnosis and prevention of cervical tumor.

SUMMARY

The claimed invention provides that a patient herself may perform the test, or that the test may be performed by a doctor. According to the claimed method, there is no need to sterilize the outer genitalia completely using a piece of cotton, resulting in a user-friendly technique. The fact that the device has a clean lubricant facilitates the entry of the device. Thanks to the accuracy mark of the claimed invention, namely, the HVS and Pap smear test apparatus, one may understand that the tissue has been touched.

The claimed invention, namely, the HVS and Pap smear test apparatus, can eliminate the disadvantages of known techniques and introduces new solutions to the problems in the known techniques.

The structural and characteristic features of the invention and all its advantages will be better understood thanks to the written explanation made below, by making reference to the figures and the detailed explanation.

REFERENCE NUMBERS ASSISTING IN EXPLANATION OF THE INVENTION

Figures 1A, 1B, 1C:
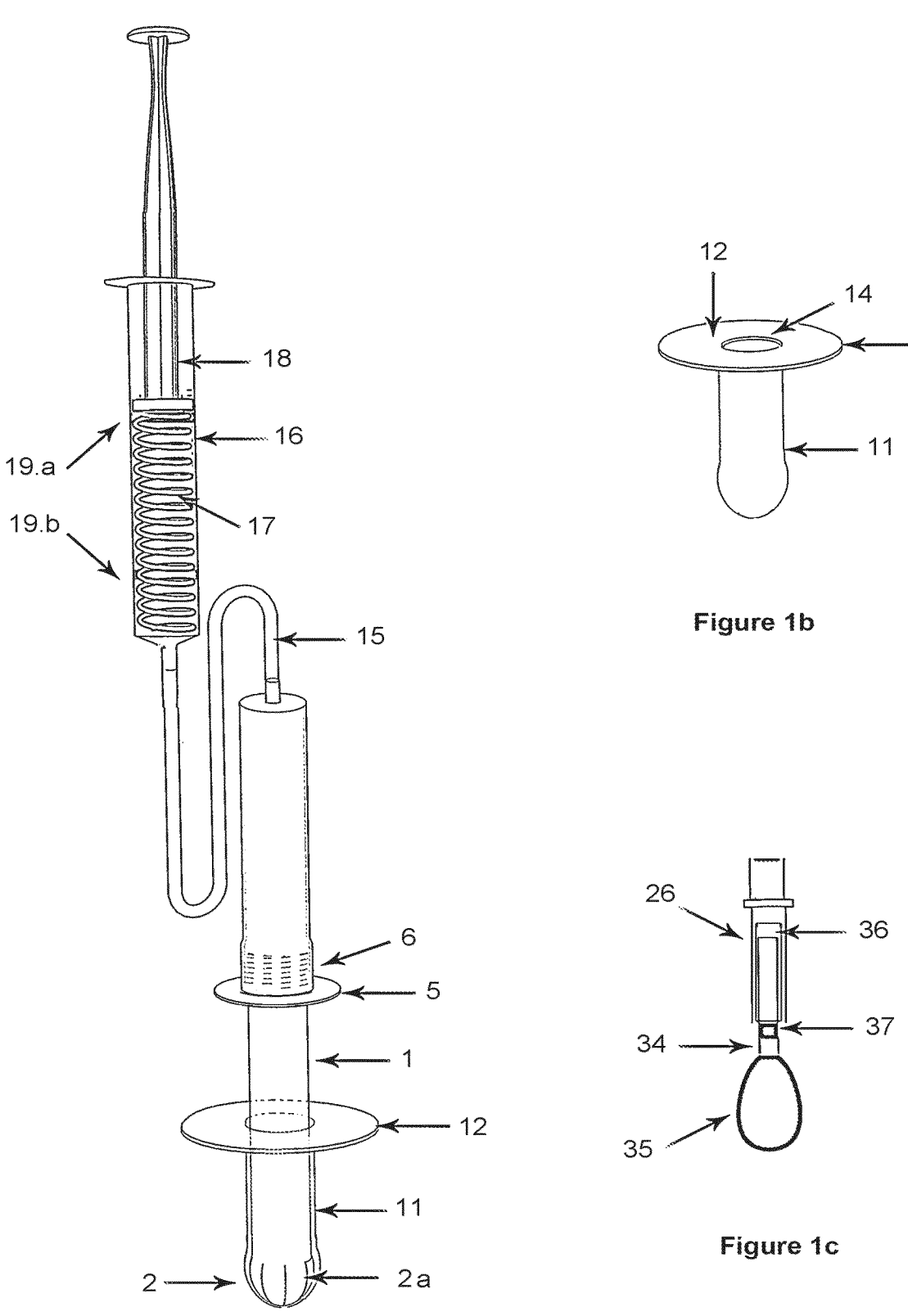
FIG. 1a is a side view of an embodiment of a cotton-tipped HVS and Pap smear testing apparatus for self-administration by a patient.
FIG. 1*b* is a side view of a protective cover for the embodiment of FIG. 1*a*.
FIG. 1*c* is a side view of a cotton tip for the embodiment of FIG. 1*a*.

1. External cylinder
2. Head
2.*a*. Petal portion
3. Inner surface

4. Outer surface
5. First outer ring
6. Threaded end
7. First inner ring
8. First internal cylinder
9. End cap
10. Piston cover
11. Protective cover
12. End part
13. Outer end side
14. Interior end side
15. Flexible tube
16. Syringe barrel
17. Third spring
18. Syringe plunger
19.*a*. First limit mark
19.*b*. Second limit mark
20. Second outer ring
21. Second inner ring
22. First spring
23. Second internal cylinder
24. Third outer ring
25. First aperture
26. Tip holder
27. Second spring
28. Recoil cylinder
29. Second aperture
30. Disk
31. Helical screw
32. Fourth outer ring
33. Fifth outer ring
34. First head bar
35. Cotton
36. Empty space
37. Accuracy mark
38. First truncated cone
39. Piston
40. Rubber cap
41. Rear end
42. Connecting tip
43. Second truncated cone
45. Extension rod
46. Second head bar
47. Brush
48. Sixth outer ring
49. Brush bristle
50. Sharp edge
51. Shaft hole

DETAILED DESCRIPTION

The embodiments disclosed herein are directed towards an HVS and Pap smear testing apparatus self-administered by women themselves or administered by doctors. The components of the embodiments of the HVS and Pap smear testing apparatus are as follows: external cylinder (1), head (2), inner surface (3), outer surface (4), first outer ring (5), threaded end (6), first inner ring (7), first internal cylinder (8), end cap (9), cylinder (10), protective cover (11), end part (12), outer end side (13), interior end side (14), flexible tube (15), syringe barrel (16), third spring (17), syringe plunger (18), first limit mark (19.*a*), second limit mark (19.*b*), second outer ring (20), second inner ring (21), first spring (22), second internal cylinder (23), third outer ring (24), first aperture (25), tip holder (26), second spring (27), recoil cylinder (28), second aperture (29), disk (30), helical screw (31), fourth outer ring (32), fifth outer ring (33), first head bar (34), cotton (35), empty space (36), accuracy mark (37), first truncated cone (38), piston (39), rubber cap (40), rear end (41), connecting tip (42), wing, second truncated cone (43), extension rod (45), second head bar (46), brush (47), sixth outer ring (48), brush bristle (49), sharp edge (50), and shaft hole (51).

Figure 4A:
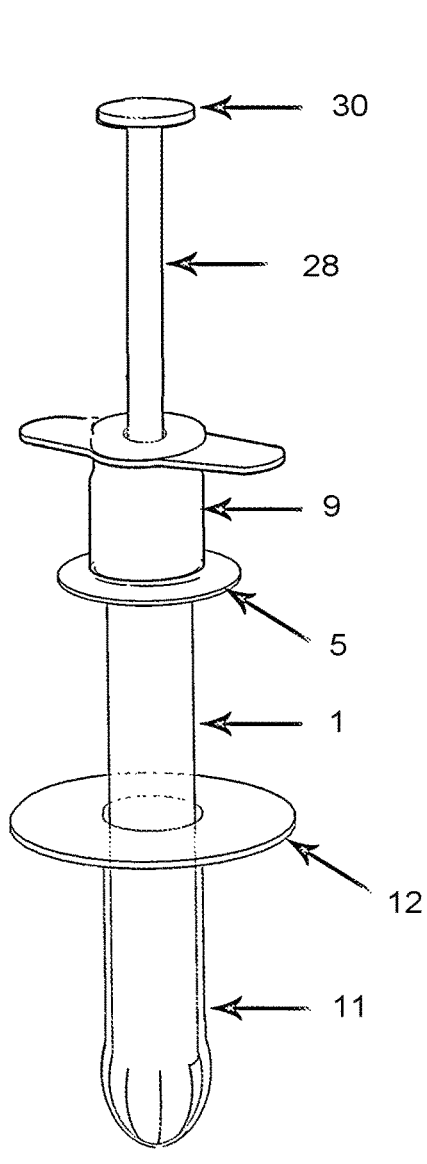
FIG. 4*a* is a side view of an embodiment of a cotton-tipped HVS and Pap smear testing apparatus for administration by a doctor.
Figure 4B:
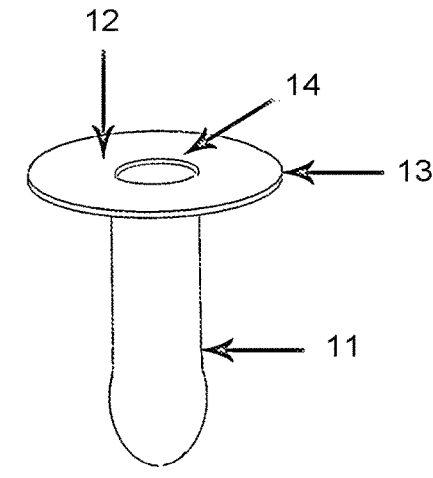
FIG. 4*b* is a side view of a protective cover for the embodiment of FIG. 4*a*.
Figure 4C:
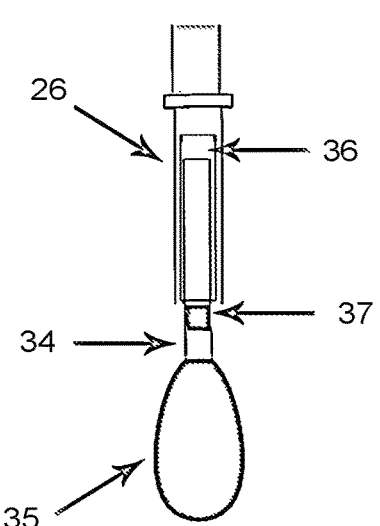
FIG. 4*c* is a side view of a cotton tip for the embodiment of FIG. 4*a*.
Figure 5A:
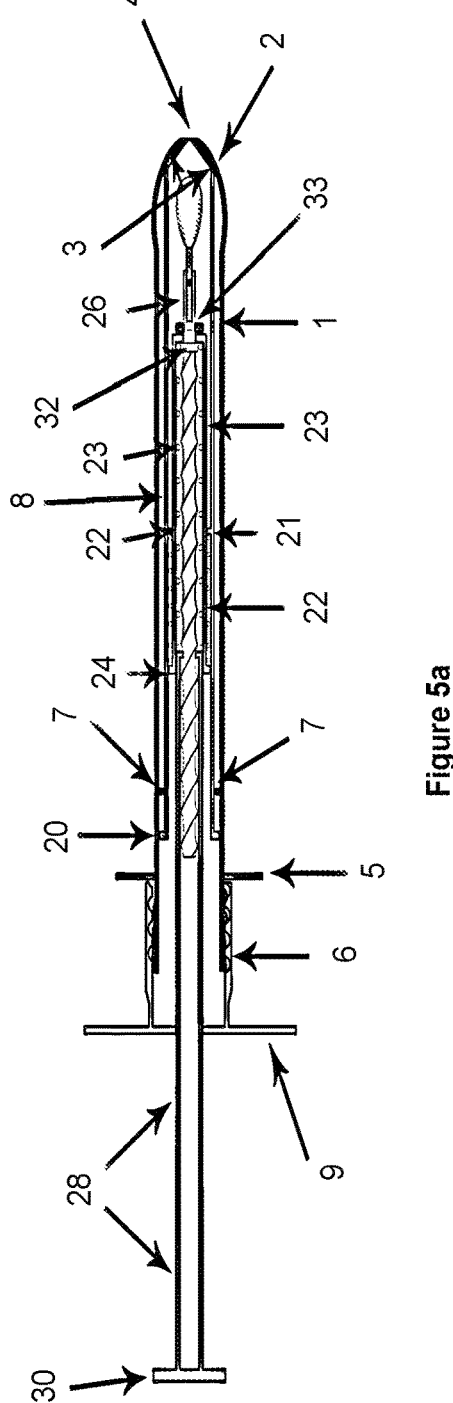
FIG. 5*a* is a cross-sectional view of the embodiment of the cotton-tipped HVS and Pap smear testing apparatus for administration by a doctor, in a closed state.
Figure 5B:
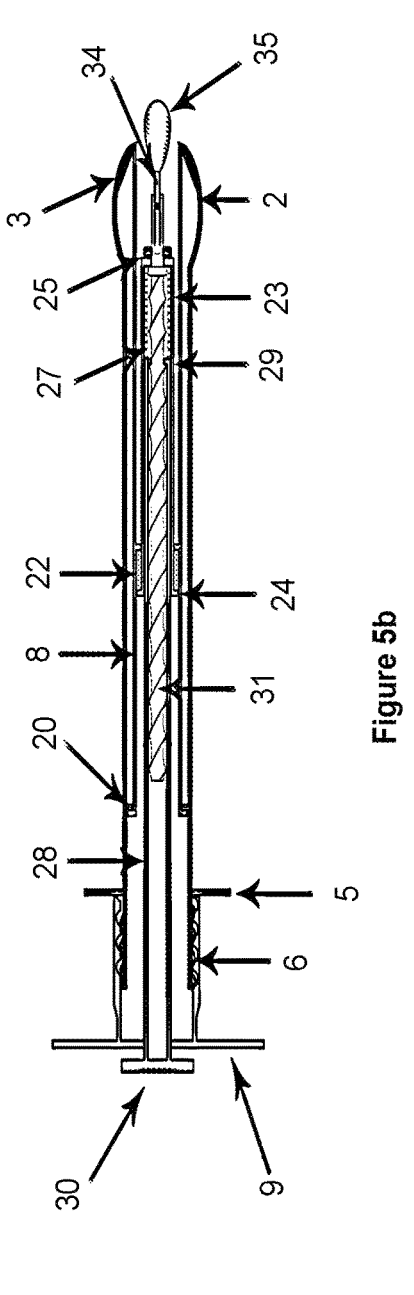
FIG. 5*b* is a cross-sectional view of the embodiment of FIG. 5*a*, in an open state.
Figure 6:
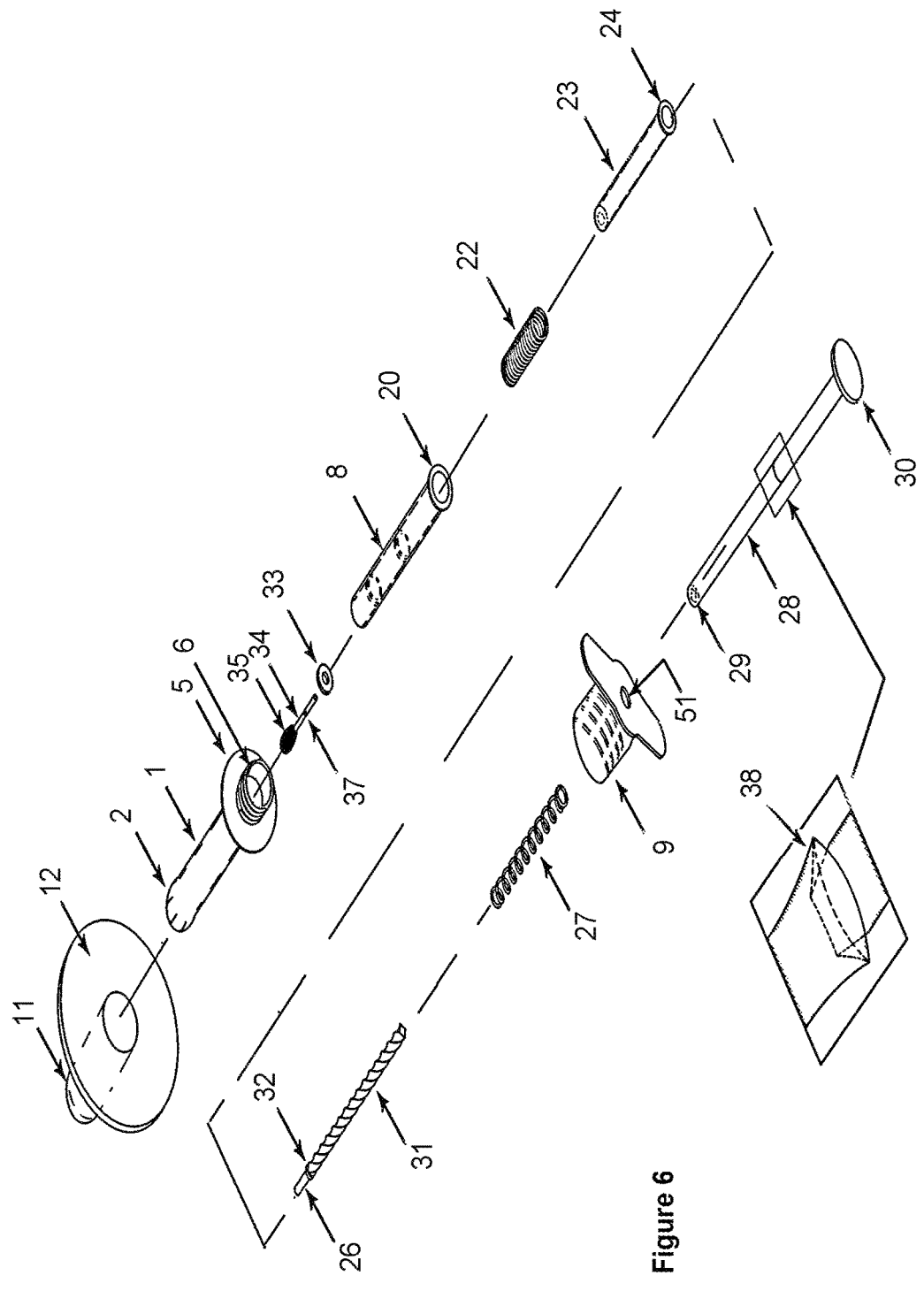
FIG. 6 is an exploded view of the embodiment of the cotton-tipped HVS and Pap smear testing apparatus for administration by a doctor.

According to an exemplary embodiment, and as shown in FIGS. 4-6, a cotton-tipped HVS and Pap smear testing apparatus for administration by a doctor is disclosed. This embodiment includes the following components:

External cylinder (1) having a diameter between 1.6 and 2.4 cm and length between 10 to 14 cm.

Head part (2) intersected lengthwise into a plurality of petal portions (2.a), disposed in front of external cylinder (1) and opening in a rose shape, A thin and flat inner surface (3) of head (2) in order for the head to come out easily, and a curved and thick outer surface (4), First outer ring (5) having a thickness of 1 to 1.2 cm surrounding the exterior of the external cylinder (1), Threaded end (6) for coupling external cylinder (1) and end cap (9), First inner ring (7) and second inner ring (21) supporting the movement of first internal cylinder (8) and second internal cylinder (23), respectively, First internal cylinder (8) slidably disposed within the external cylinder (1), End cap (9) intermeshing with threaded end (6), Second outer ring (20) having a protrusion of 1 mm, which limits the movement of the first internal cylinder (8), First spring (22) provided between the first inner ring (7) and third outer ring (24), Second internal cylinder (23), closed at the proximal end and disposed inside first internal cylinder (8), and provided with a hole for receiving the head in the center thereof, Third outer ring (24) abutting first spring (22) at the distal end of second internal cylinder (23), First aperture (25) for receiving the tip holder (26) in the proximal end of the helical screw (31), Tip holder (26) with an open proximal end for receiving the cotton (35) head Second spring (27) available inside the second internal cylinder (23), Recoil cylinder (28) for providing pressure by the doctor to the HVS and Pap smear testing apparatus, Second aperture (29) having a square shape, defined at the proximal end of recoil cylinder (28) and receiving helical screw (31) therein, Disk (30), coupled to the distal end of recoil cylinder 28, for pushing the recoil cylinder by the thumb of the doctor, First truncated cone (38) preventing the recoil cylinder 28 from being withdrawn after sample is taken, Shaft hole (51) for receiving recoil cylinder 28 through end cap (9), Helical screw (31) received in the square second aperture (29) defined in the recoil cylinder (28), Fourth outer ring (32) between the helical screw (31) and tip holder (26), Fifth outer ring (33) to fix the tip holder (26), First head bar (34) in the shape of a toothpick, Cotton (35) in the proximal end of first head bar (34), Empty space (36) ensuring controlling that sample is taken with the movement of first head bar (34) when pressure is applied to HVS and Pap smear testing apparatus within tip holder (26), The accuracy mark (37) serving to control that sample has been taken after disappearance of red line on the apparatus by the apparatus contacting the edge when pushed toward the empty space (36) after applying pressure to HVS and Pap smear testing apparatus.

Figures 2A, 2B:
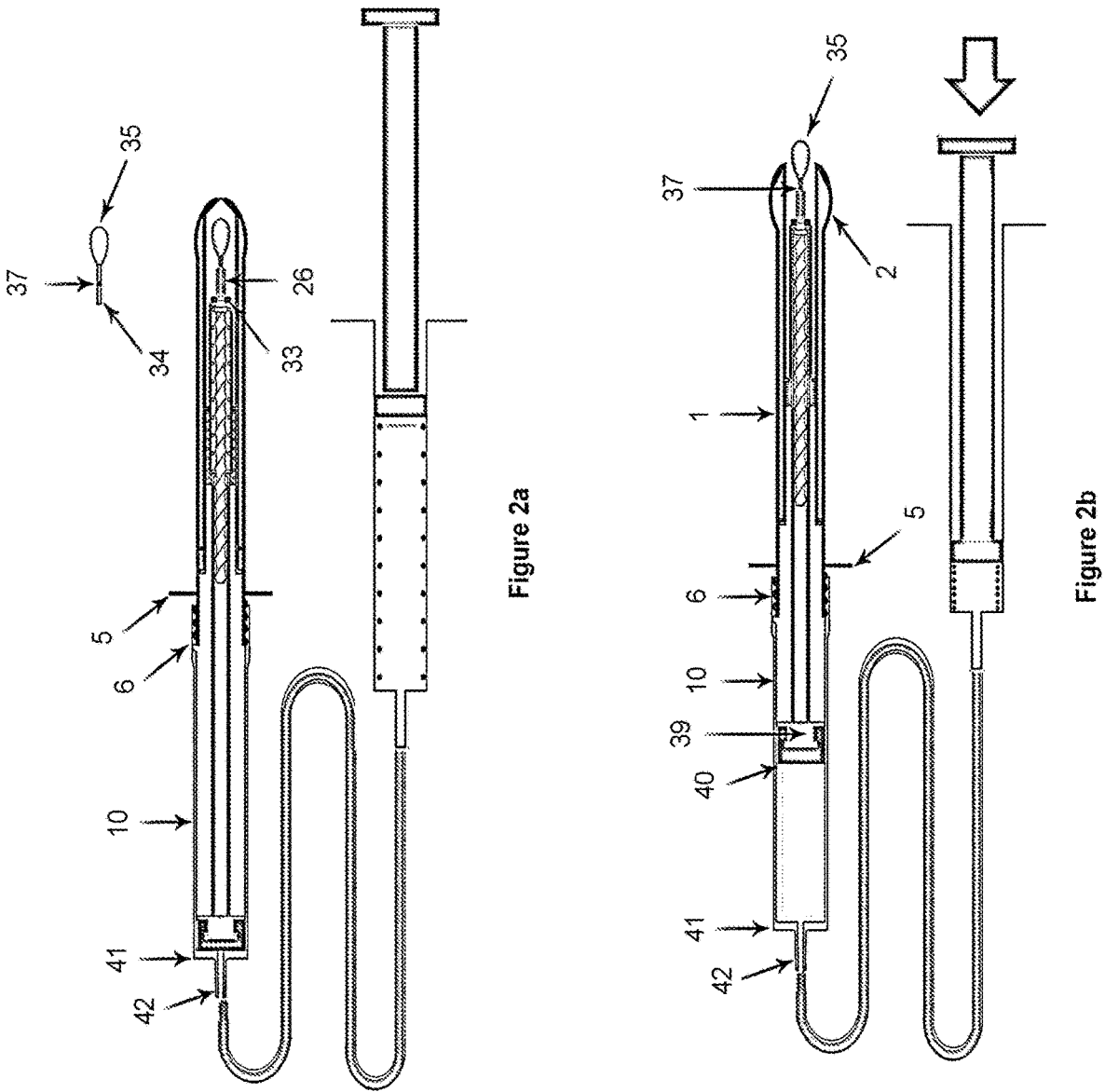
FIG. 2*a* is a cross-sectional view of the embodiment of the cotton-tipped HVS and Pap smear testing apparatus for self-administration by a patient, in a closed state.
FIG. 2*b* is a cross-sectional view of the embodiment of FIG. 2*a*, in an open state.
Figure 3:
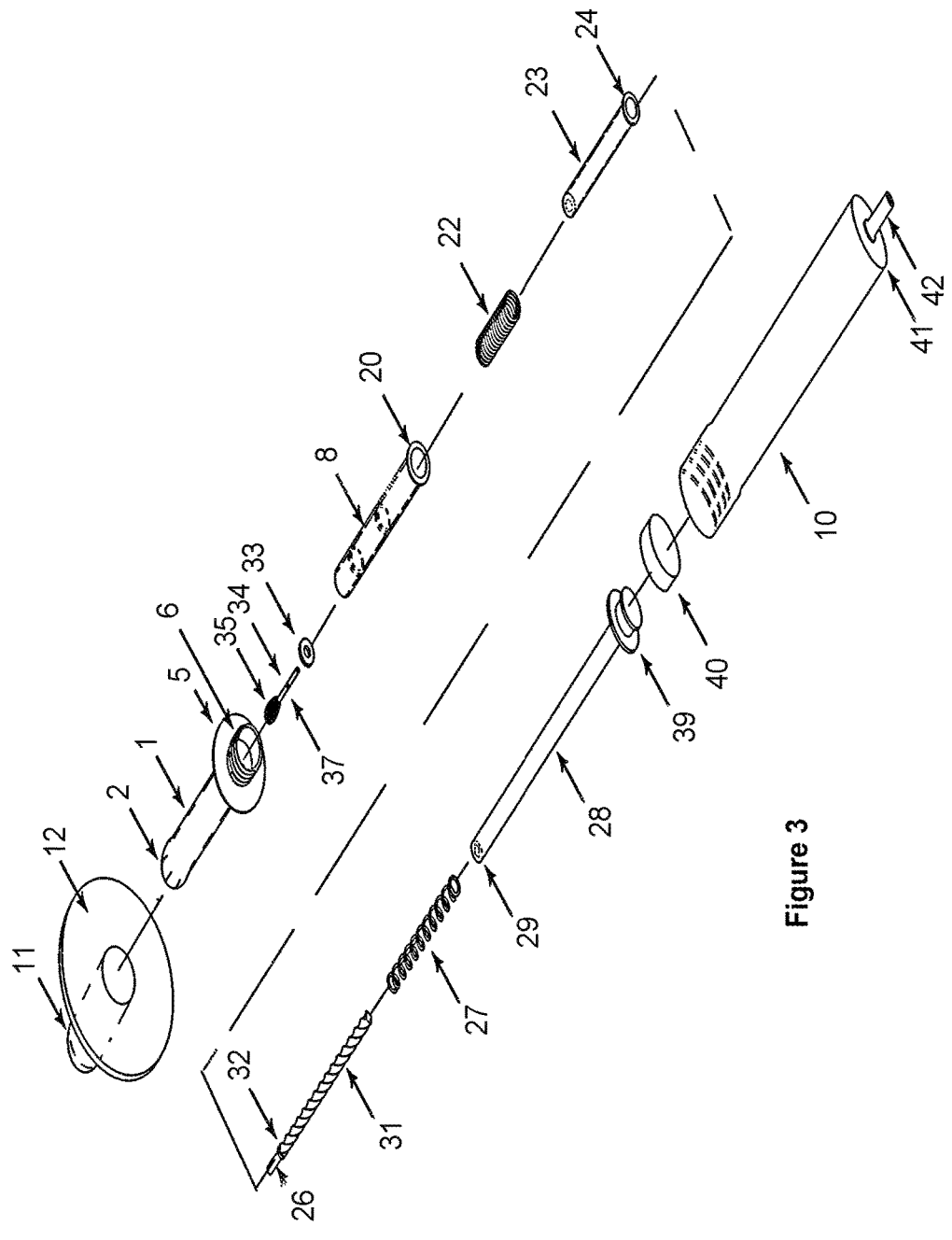
FIG. 3 is an exploded view of the embodiment of the cotton-tipped HVS and Pap smear testing apparatus for self-administration by a patient.
Figures 7A, 7B, 7C:
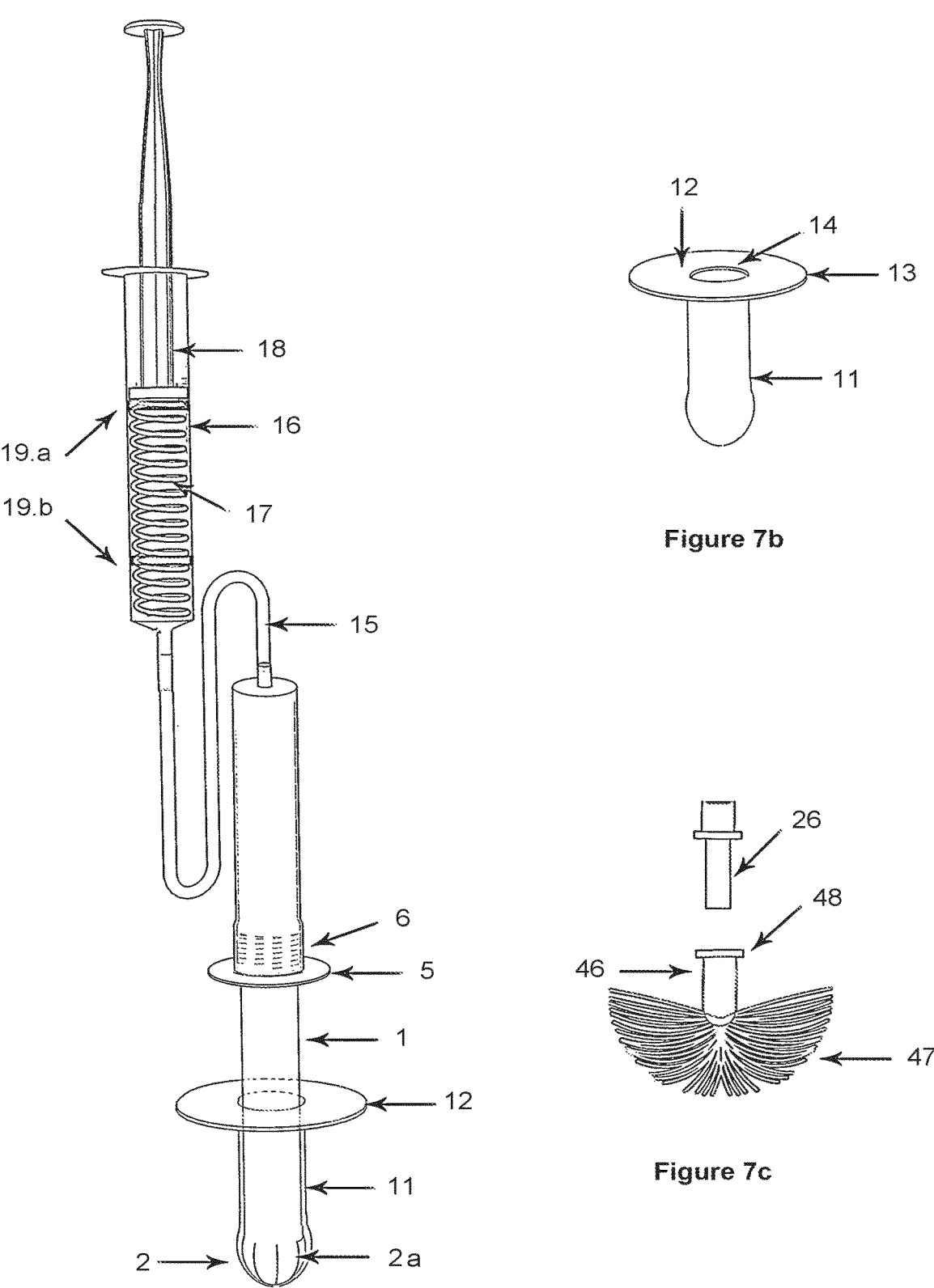
FIG. 7*a* is a side view of an embodiment of a brush-tipped HVS and Pap smear testing apparatus for self-administration by a patient.
FIG. 7*b* is a side view of a protective cover for the embodiment of FIG. 7*a*.
FIG. 7*c* is a side view of a brush tip for the embodiment of FIG. 7*a*.
Figures 8A, 8B, 8C:
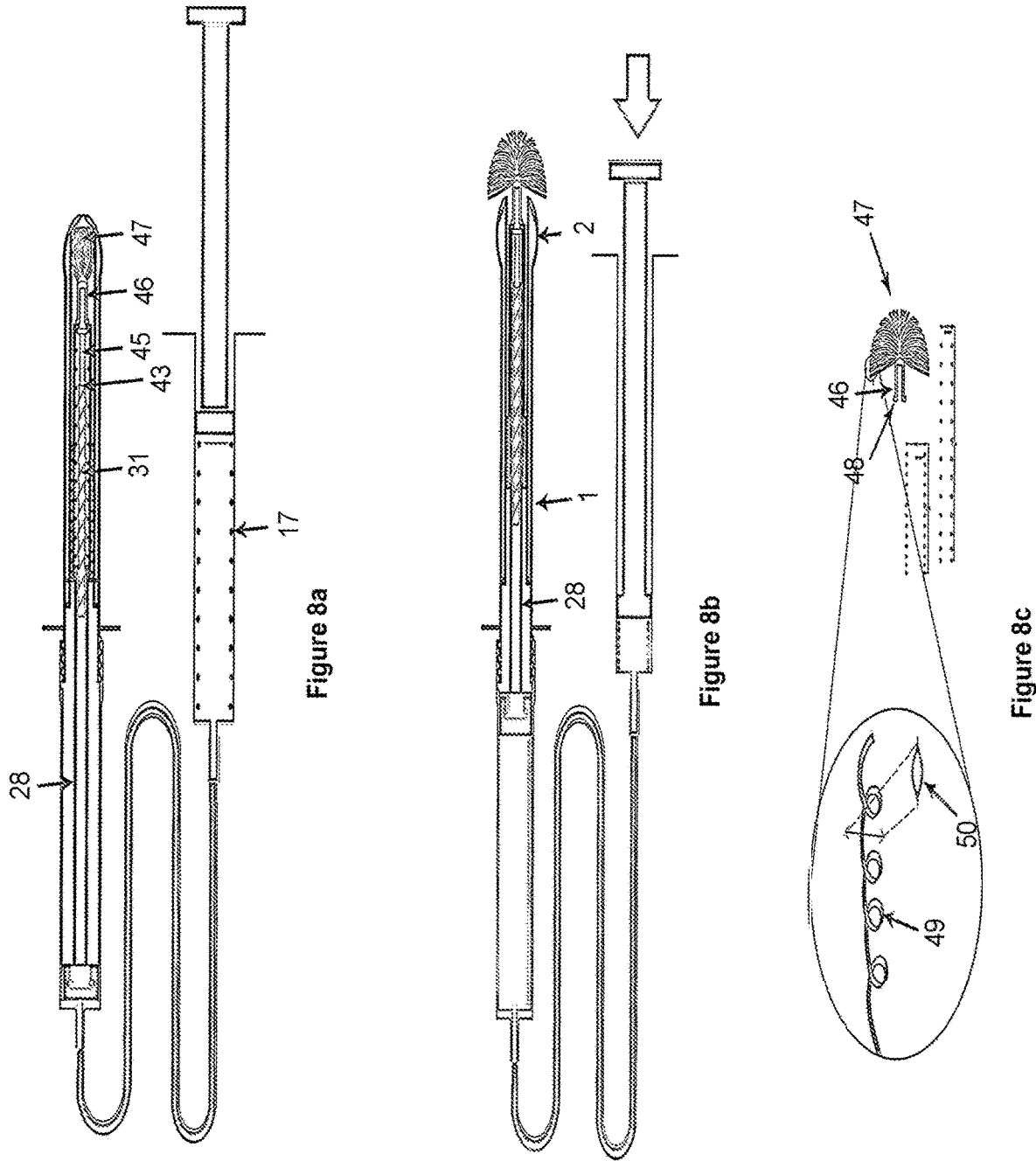
FIG. 8*a* is a cross-sectional view of the embodiment of the brush-tipped HVS and Pap smear testing apparatus for self-administration by a patient, in a closed state.
FIG. 8*b* is a cross-sectional view of the embodiment of FIG. 8*a*, in an open state.
FIG. 8*c* is a detailed cross-sectional view of the brush tip of the embodiment of FIG. 8*a*.
Figure 9:
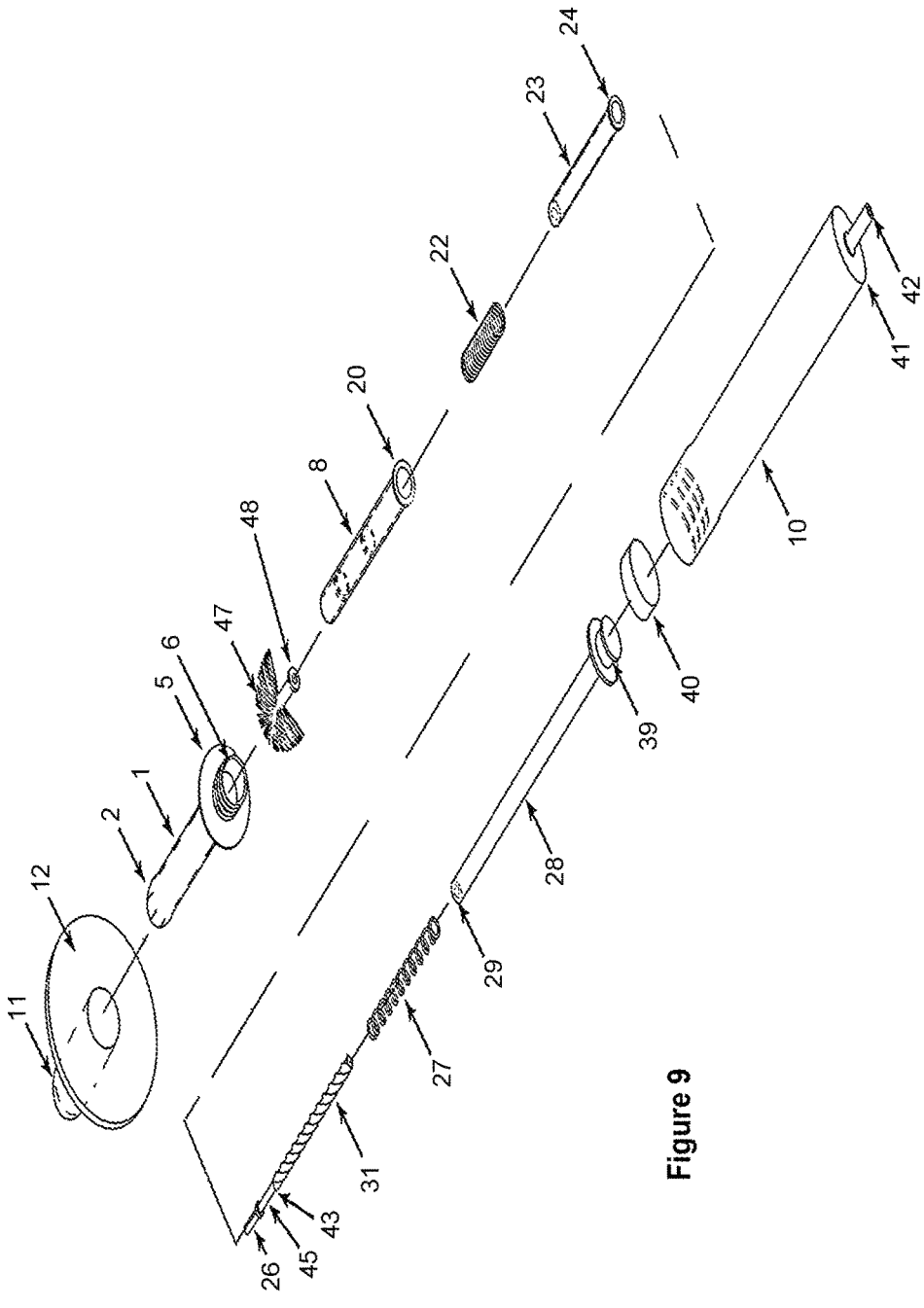
FIG. 9 is an exploded view of the embodiment of the brush-tipped HVS and Pap smear testing apparatus for self-administration by a patient.

According to another exemplary embodiment, and as shown in FIGS. 1-3, a cotton-tipped HVS and Pap smear testing apparatus for self-administration by a patient is disclosed. According to another exemplary embodiment, and as shown in FIGS. 7-9, a brush-tipped HVS and Pap smear testing apparatus for self-administration by a patient is disclosed. These embodiments include the following components that are different from the embodiments for administration by a doctor:

Piston cover (10) integrated with external cylinder (1) in the HVS and Pap smear testing apparatus for self-administration by the patient, Piston (39) provided instead of disk (30) at the distal end of the recoil cylinder (28), Rubber cap (40) integrated with the piston (39), A closed rear end (41) disposed at the distal end of the piston cover (10), Connecting tip (42) passing through the center of the rear end (41), Flexible tube (15) allowing for a movement of piston cover (10) and syringe barrel (16) relative to each other, having a length between 25 cm to 40 cm, and connected to the connecting tip (42), Syringe barrel (16) connected to flexible tube (15), Third spring (17) ensuring that the HVS and Pap smear testing apparatus reverts to its previous position subsequent to pressure applied by patient, disposed inside the syringe barrel (16), Syringe plunger (18) providing for pressure to be applied by the patient, First limit mark (19.a) and second limit mark (19.b) providing guidance that the procedure has been done correctly when pressure is applied by the patient to syringe plunger (18), disposed on the syringe barrel (16) and delimiting the start and end positions of the syringe plunger.

Figure 10A:
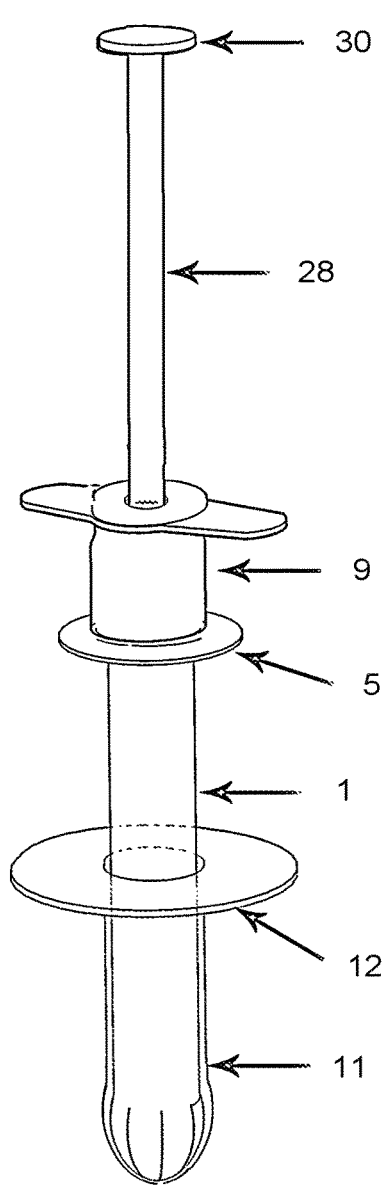
FIG. 10*a* is a side view of an embodiment of a brush-tipped HVS and Pap smear testing apparatus for administration by a doctor.
Figure 10B:
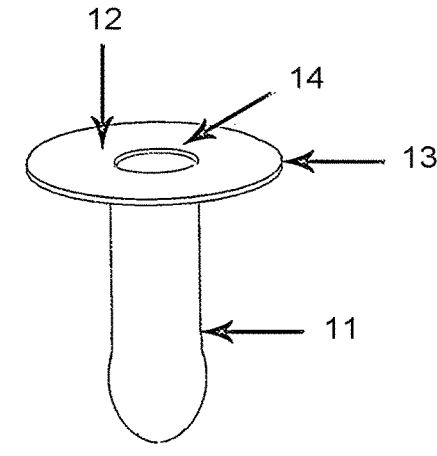
FIG. 10*b* is a side view of a protective cover for the embodiment of FIG. 10*a*.
Figure 10C:
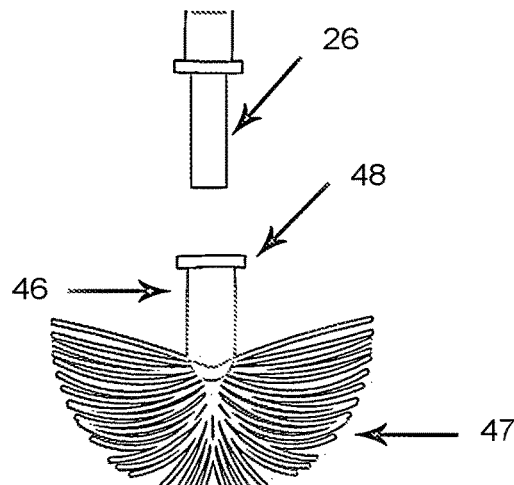
FIG. 10*c* is a side view of a brush tip for the embodiment of FIG. 10*a*.
Figure 11A:
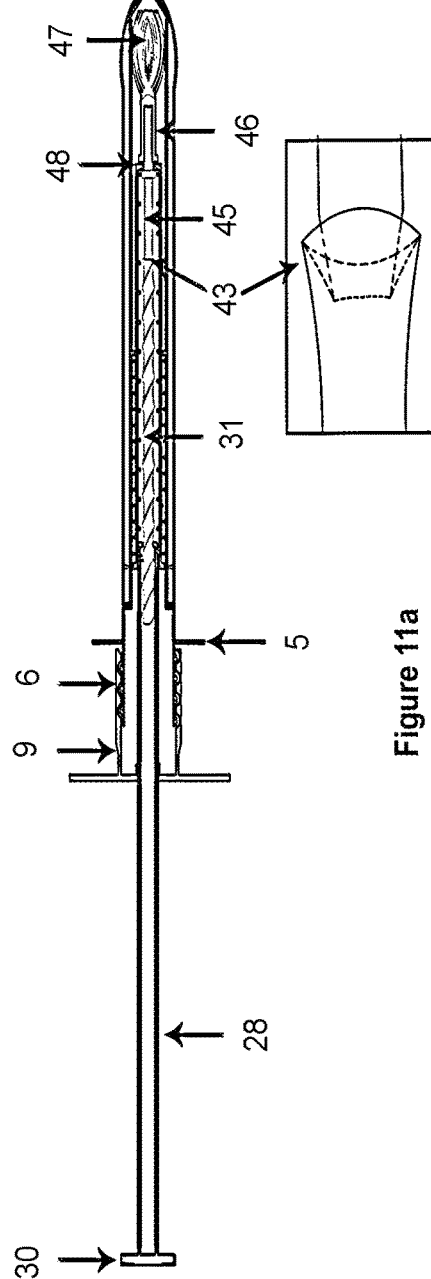
FIG. 11*a* is a cross-sectional view of the embodiment of the brush-tipped HVS and Pap smear testing apparatus for administration by a doctor, in a closed state.
Figure 11B:
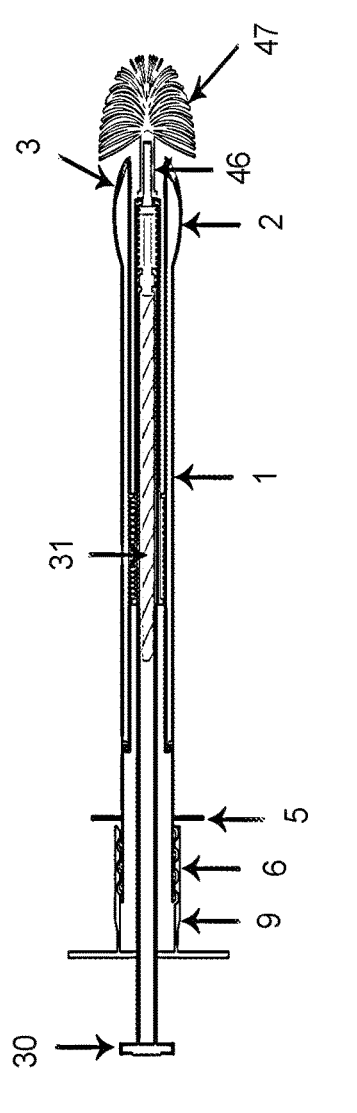
FIG. 11*b* is a cross-sectional view of the embodiment of FIG. 11*a*, in an open state.
Figure 12:
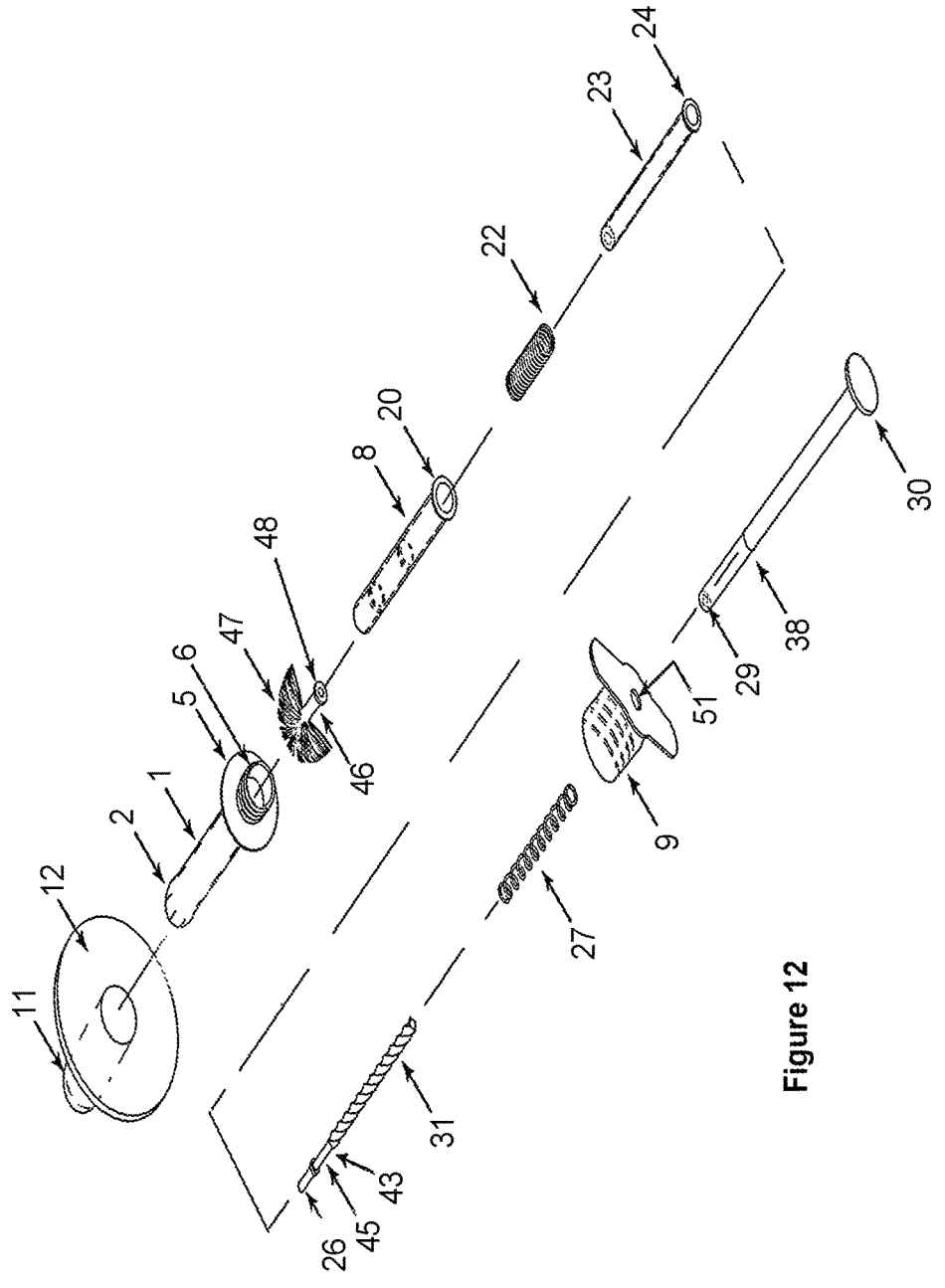
FIG. 12 is an exploded view of the embodiment of the brush-tipped HVS and Pap smear testing apparatus for administration by a doctor.

According to another exemplary embodiment, and as shown in FIGS. 10-12, a brush-tipped HVS and Pap smear testing apparatus for administration by a doctor is disclosed. This embodiment, and the embodiment of the brush-tipped apparatus for self-administration by a patient, include the following components that are different from the cotton-tipped embodiments:

Wing ensuring that the brush-tip (47) rotates a complete rotation,

Second truncated cone (43) allowing for the recoil cylinder (28) to pass through the second aperture (29) in one direction, Extension rod (45) providing for further movement of the brush tip (47) at the end of the wing, Sixth outer ring (48) fixing the tip holder (26), locking the system, facilitating the procedure of taking the sample and ensuring rotation in a single direction, Second head bar (46) integrated with sixth outer ring (48), Brush (47) at the end of second head bar (46), Longer first spring (22) provided between first inner ring (7) and third outer ring (24) for the brush (47) to rotate more, Longer second spring (27) provided inside the second internal cylinder (23), being longer for the brush (47) to rotate more, Tip holder (26) with an end closed coupled to the brush (47), Spiral and transverse cross-sectioned brush (47) bristle (49), A sharp edge (50) of the brush (47) bristle (49) ensuring that cell is taken from the cervix easily.

All four embodiments disclosed herein include the following components:

Protective cover (11) mountable onto the head (2) and manufactured from latex, providing a very thin and soft material wrapping the head, which is slippery and has a length of 4 cm, Curved outer edge side (13) and sloped interior edge side (14) in the edge side (12) of the protective cover (11).

The claimed invention may be self-administered by a patient or administered by a doctor. The device provides the convenience of being able to take a cervical cell sample for Human Papilloma Virus (HPV) and culture sensitivity or liquids from deep in the vagina. According to exemplary embodiments, a brush tip (47) is used for taking cervical cell samples and a cotton tip (35) is used for sampling liquids from the vagina.

When pressure is applied to recoil cylinder (28) in the tip end direction, first internal cylinder (8) moves toward the tip end of external cylinder (1), thereby opening head (2) into the open-petal shape, second internal cylinder (23) moves toward the tip end of first internal cylinder (8), and recoil cylinder (28) moves toward the tip end of second internal cylinder (23), thereby rotating helical screw (31) and the cotton tip (35) or brush tip (47). The cotton tip (35) or brush tip (47) takes a sample from the relevant area and then recedes into the cylinder; the head part of the cylinder closes after the retreat of the tip. Thus, contact between the obtained sample and other areas is prevented. In order to be able to take the sample easily from the protruding cervix, the brush (47) bristles (49) are helical and long, with a sharp edge. The brush can execute a complete rotation while the sample is being taken due to the rotation of the helical screw (31).

The claimed invention easily reaches the necessary depth due to its lubricity. The flexible protective cover (11) is adapted to being torn easily by way of force applied by the protruding tip and expanding head. During the procedure, injury to the patient may be prevented by monitoring that the HVS and Pap smear testing apparatus reaches the necessary depth by reference to the first limit mark (19.*a*) and second limit mark (19.*b*) on the syringe barrel (16). After the pressure is applied to the cotton (35) tip, the red line on the accuracy mark (37) disappears. Thus, referring to the accuracy mark (37) provide assurance that a sample has been taken.

The invention ensures that the head part (2) opens by applying force to external cylinder (1) from flexible tube (15) by means of a push applied manually to syringe plunger (18) in the embodiment of the HVS and Pap smear testing apparatus for self-administration. The sample taken from the cervix and within the vagina is capable of reaching the laboratory without contact with other surfaces.

The advantages of the claimed invention:

It does not give rise to any pain or discomfort in the area of the vagina.

Due to the outer side of the head part (2) of the HVS and Pap smear testing apparatus being curved and ragged, no pain is caused when the head part is pushed into and within the vagina.

When the procedure is concluded, the HVS and Pap smear testing apparatus closes on its own.

When the targeted tissue is touched, the red line in the accuracy mark (37) disappears, which enables confirmation that the sample has been taken.

The HVS and Pap smear testing apparatus may be mounted with a single hand and directed with the other, due to the flexible tube (15) inside the vagina, The HVS and Pap smear testing apparatus is sterile due to the protective cover (11), The HVS and Pap smear testing apparatus performs sufficient contact to the cervix due to the automatic rotation of the brush (47) tip.

The foregoing description and accompanying figures illustrate the principles, preferred embodiments and modes of operation of the invention. However, the invention should not be construed as being limited to the particular embodiments discussed above. Additional variations of the embodiments discussed above will be appreciated by those skilled in the art.

Therefore, the above-described embodiments should be regarded as illustrative rather than restrictive. Accordingly, it should be appreciated that variations to those embodiments can be made by those skilled in the art without departing from the scope of the invention as defined by the following claims.

The invention claimed is:

1. A HVS and pap smear testing devise comprising:

an external cylinder having a proximal end and a threaded distal end;

a head disposed at the proximal end of the external cylinder, the head being subdivided into a plurality of petal portions;

a first internal cylinder slidably disposed within the external cylinder;

a second internal cylinder slidably disposed within the first internal cylinder;

a recoil cylinder having at least a portion thereof slidably disposed within the second internal cylinder, the recoil cylinder being provided with an aperture at a proximal end thereof;

a helical screw having a proximal end rotatably mounted at a proximal end of the second internal cylinder and extending into the recoil cylinder via the aperture, wherein the aperture is sized and shaped so as to cause a rotation of the helical screw when the recoil cylinder is moved relative to the helical screw;

a tip coupled to the proximal end of the helical screw via an aperture defined at the proximal end of the second internal cylinder;

wherein the external cylinder, the first internal cylinder, the second internal cylinder, the recoil cylinder, and the helical screw are mounted coaxially to each other;

wherein, when the recoil cylinder is caused to move along a direction from the distal end of the external cylinder to the proximal end of the external cylinder, the first internal cylinder moves toward the proximal end of the external cylinder, thereby opening the head into an open-petal shape, the second internal cylinder moves toward the proximal end of the first internal cylinder, and the recoil cylinder moves toward the proximal end of the second internal cylinder, thereby rotating the helical screw and the tip.

2. The HVS and pap smear testing device of claim 1, further comprising a head bar and a tip holder, wherein a distal end of the tip is coupled to a proximal end of the head bar, a distal end of the head bar is coupled to a proximal end of the tip holder, and a distal end of the tip holder is coupled to the proximal end of the helical screw.

3. The HVS and pap smear testing device of claim 2, wherein:

the tip is a cotton tip;

the head bar includes an accuracy mark defined on an outer surface thereof; and when pressure is applied to the cotton tip, the distal end of the head bar is moved into an interior bore of the tip holder such that the accuracy mark is obscured by the tip holder.

4. The HVS and pap smear testing device of claim 2, wherein:

the tip is a brush tip;

the distal end of the tip holder is coupled to the proximal end of the helical screw via an extension rod; and the brush tip radially expands during rotation so as to remove cells from a cervix.

5. The HVS and pap smear testing device of claim 1, further comprising:

an end cap threadably coupled to the threaded distal end of the external cylinder;

a shaft hole defined through a distal end of the end cap; and a disk disposed at a distal end of the recoil cylinder;

wherein the recoil cylinder passes through the shaft hole of the end cap; and wherein pressure applied to the disk causes the recoil cylinder to move along the direction from the distal end of the external cylinder to the proximal end of the external cylinder.

6. The HVS and pap smear testing device of claim 1, further comprising:

a piston cover, threadably coupled to the threaded distal end of the external cylinder and having an interior defined therein, the interior being in fluidic communication with an interior of the external cylinder;

a piston, having at least a portion thereof formed from rubber, disposed at a distal end of the recoil cylinder and slidably movable within the interior of the piston cover;

a syringe barrel fluidically coupled via a flexible tube to the interior of the piston cover; and a syringe plunger slidably disposed in the barrel, and resiliently biased relative to the barrel;

wherein pressure applied to the syringe plunger causes the recoil cylinder to move along the direction from the distal end of the external cylinder to the proximal end of the external cylinder.

7. The HVS and pap smear testing device of claim 1, wherein the second internal cylinder is resiliently biased with respect to the first internal cylinder, and the recoil cylinder is resiliently biased with respect to the second internal cylinder.

8. The HVS and pap smear testing device according to claim 1, further comprising a protective cover removably mounted onto the head.

9. The HVS and pap smear testing device of claim 5, further comprising a truncated cone defined on an external surface of the recoil cylinder, the diameter of the truncated cone increasing towards a rear end of the recoil cylinder, the truncated cone being sized and shaped to pass through the shaft hole of the end cap only in the direction from the distal end of the external cylinder to the proximal end of the external cylinder.

10. The HVS and pap smear testing device of claim 1, wherein:

the external cylinder includes a first outer ring located proximate the distal end of the external cylinder and a first inner ring located within the external cylinder;

the first internal cylinder includes a second outer ring at a distal end thereof and a second inner ring within said first internal cylinder, and is supported within the external cylinder by the first inner ring and the second outer ring; and the second internal cylinder includes a third outer ring at a distal end thereof, and is supported within the first internal cylinder by the second inner ring and the third outer ring.

11. The HVS and pap smear testing device of claim 10, further comprising:

a first spring disposed between the second inner ring and the third outer ring; and a second spring disposed within the second internal cylinder between the proximal end of the second internal cylinder and the proximal end of the recoil cylinder.

* * * * *